United States Patent [19]

Pinheiro

[11] Patent Number: 4,896,767

[45] Date of Patent: Jan. 30, 1990

[54] SUTURE PACKAGE

[75] Inventor: Ricardo L. M. Pinheiro, Sao Paulo, Brazil

[73] Assignee: Ethicon, Inc., Somerville, N.J.

[21] Appl. No.: 327,857

[22] Filed: Feb. 9, 1989

[30] Foreign Application Priority Data

Feb. 9, 1988 [BR] Brazil .................................. 8800527

[51] Int. Cl.⁴ .............................................. A61L 15/00
[52] U.S. Cl. ................................... 206/63.3; 206/476; 206/484
[58] Field of Search ....................... 206/63.3, 476, 484, 206/628, 227

[56] References Cited

U.S. PATENT DOCUMENTS

| | | | |
|---|---|---|---|
| 4,135,623 | 1/1979 | Thyen | 206/63.3 |
| 4,253,563 | 3/1981 | Komarnycky | 206/63.3 |
| 4,391,365 | 7/1983 | Batchelor | 206/63.3 |
| 4,483,437 | 11/1984 | Cerwin et al. | 206/63.3 |
| 4,572,362 | 2/1986 | Alpern | 206/63.3 |
| 4,615,435 | 10/1986 | Alpern | 206/63.3 |

Primary Examiner—Joseph Man-Fu Moy

[57] ABSTRACT

The present invention refers to a suture package of the folded type for a plurality of single or double sutures, characterized by comprising two suture-mounting panels (11,13) and one interconnection panel (12), the sutures (23) being individually mounted on the two suture-mounting panels (11,13) by fixing the needle (24) or the suture (23) immediately adjacent to the needle on a supporting and holding element (14) arranged adjacent to one end of each mounting panel (11,13) each suture-mounting panel possessing at least another supporting and holding element (14) used to fix the suture thread along the mounting panel, each mounting panel (11,13) being formed with a cover flap (16,16') adapted to fold over and enclose the needles (23) when the loaded package (10) is folded to enclose the suture threads, the supporting and holding elements (14) on the two suture-mounting panels (11,13) being arranged in a displaceable manner to provide an upper row of sutures on a lower row of sutures.

6 Claims, 1 Drawing Sheet

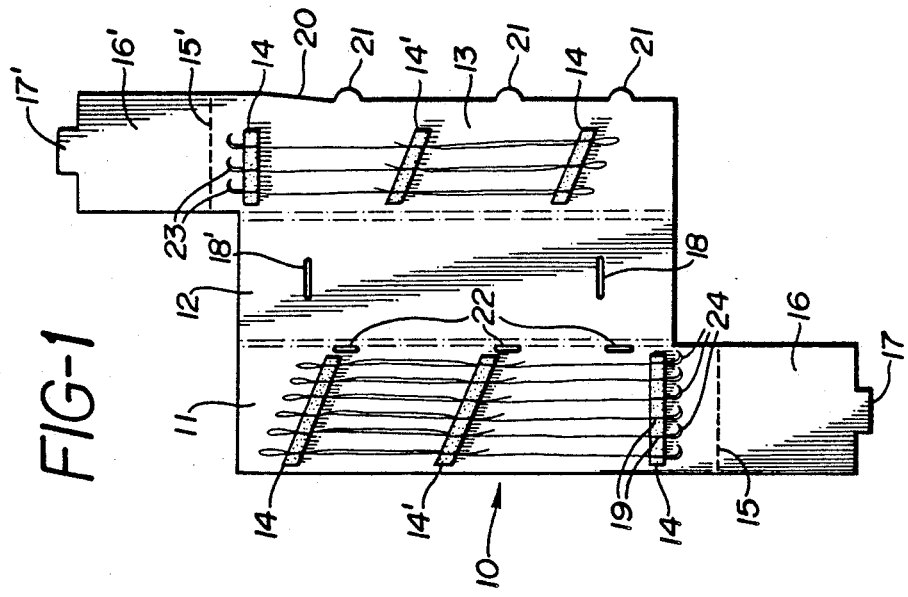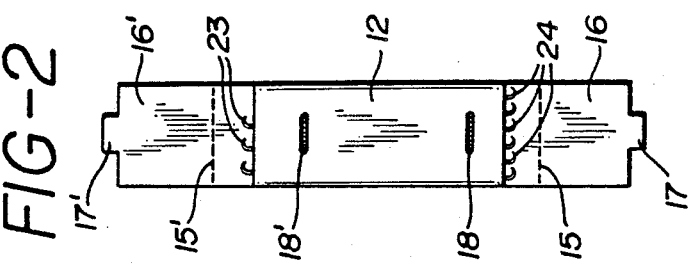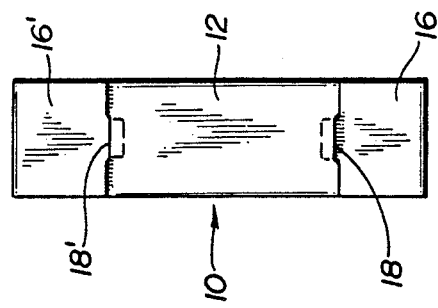

SUTURE PACKAGE

The present invention refers to a package for surgical sutures, and more specifically to folded cardboard packages to the availability of material for the user in the various kinds of coronary surgeries with two, three or more by-passes.

Packages for surgical sutures are made in accordance with the type of the suture and its specific application. Usually, packages for sutures are provided so as to make the suture easily accessible to the surgeon with a minimum of handling. This requires that the suture be packed in a manner that allows the package to be opened and the suture to be easily taken out, without entangling the suture on itself or with adjacent ones. It is also appropriate for the suture to have a minimum of folds, turns and no trend to become entangled after its is removed. In packing armed or needle-provided sutures, it is appropriate that the needles be easily accessible and, in the case of sutures with two needles, that the needles of the individual sutures be kept in pairs, so that the sutures can be taken out of the package by picking either or both needles.

As used here, the term "suture" means an elongated threadlike string appropriate for suturing, connecting or for other surgical procedures, with or without attached needles. The expression "single-leg suture" stands for a suture having one needle attached at one end, while the expression "two-leg suture" means a suture having needles attached at both ends. The expression "suture thread" refers specifically to the threadlike, elongated part of the suture. Also, the sutures can be made of course, of any suitable material such as, for example silk, cotton wire and several types of plastics, absorbable or non-absorbable by the body or any other material.

Previously armed sutures have been packed in several ways with a view to minimizing the formation of folds, turns and rolls. For instance, sutures with two needles or doubly armed sutures have been rolled in the form of a figure eight and packed in accordance with the teachings of U.S. Pat. No. 3,759,376. The package of that patent is particularly appropriate for use with rigid suture materials, more specifically those that tend to consolidate in the embodiment of the suture in the package.

The U.S. Pat. No. 3,985,227 describes a package specifically designed for thin cardiovascular sutures having relatively small needles mounted on polymeric removable blocks. The package of the present invention is also appropriate particularly for doubly armed cardiovascular sutures or sutures with two needles consisting of a flexible, light suture material and small curved needles.

Consequently, one of the object of the present invention is to provide a package for mounting a plurality of armed sutures.

Another object of the present invention is to provide a package for a plurality of doubly armed cardiovascular sutures for surgeries with one or mode by-passes, which permits an easy access and the removal of individual sutures.

A further object of the present invention is to provide a package for a plurality of armed sutures comprising a single-piece self-locking folded construction. These and other objects will be evidenced by the following description and the claims.

According to the present invention, these objects are achieved by providing a folded package for a plurality of single or double sutures comprising two suture-mounting panels and one interconnection panel, the sutures being individually mounted on the two suture-mounting panels by fixing the needle or the suture immediately adjacent the needle on a first supporting and holding element arranged adjacent to an end of each mounting panel, each suture-mounting panel formed with a cover flap adapted to fold over and enclose the needles when the loaded package is folded to enclose the suture threads, the supporting and holding elements on the two suture mounting panels being arranged in a displaceable manner, so as to provide an upper row of sutures on another lower row of sutures.

When the package is opened, the upper parts of each suture-mounting panel are exposed to display the needles, while the longest part of the suture thread remains enclosed between the package panels.

The present invention will now be described in greater detail, by way of non-limiting example, by referring to its embodiment illustrated in the accompanying drawings, in which:

FIG. 1 is a plane view of a package loaded before the folding;

FIG. 2 is a plane view of the package of FIG. 1, folded and with the cover flaps opened; and FIG. 3 is a plane view similar to FIG. 2, with the cover flaps closed.

The suture packages of the present invention comprise the three-panel, single-piece folded construction that provides two suture-mounting panels and one intermediate panel. Each suture-mounting panels is provided, at the ends and at an intermediate point between the ends, with a supporting and holding element in the form of a plastic-foam strip being as broad as the panel and provided with slots for fixing the needle-armed ends of the sutures. The foam strip of one of the ends is fixed parallel to the fold line, while the intermediate strips and that of the other end are parallel to each other by inclined with respect to the strip of the first end.

Each suture-mounting panel is stretched to form a cover flap that can be folded forwards to enclose the needle-displaying area, and appropriate interclosing tabs are provided along the edges of the panels to lock the package in the folded embodiment through slots in the intermediate panel.

One of the mounting panels possesses tabs along its length, which permits locking the package through slots existing along the other mounting panel.

FIG. 1 illustrates a preferred embodiment of the package of the present invention generally indicated under 10, composed of panels 11, 12 and 13.

A first suture mounting panel 11 extends beyond the fold line 15 to form the cover flap 16, having a tab 17 adapted to be received in the slot 18 of an interconnecting panel 12 when the package is folded and closed.

A second suture mounting panel. 13, at the opposite end of first panel 11, also extends beyond the fold line 15' to form the cover flap 16' having a tab 17' adapted to be received in the slot 18' of the interconnecting panel 12.

The dimension of the width of the second panel 13 along its free side edge is rescued through the inclined line 20 to permit the formation of three interclosing tabs 21 to lock the package in the folded embodiment through corresponding slots 22 formed in the first panel 11.

Panels 11 and 13 are provided with three plastic-foam strips 14, 14', located at the ends and at an intermediate point of each panel. The strip 14 near the flap 16 on first panel 11 is parallel to the fold line 15, and the others 14, 14', which are parallel to each other, are inclined with respect to the strip 14 of the end adjacent to the flap 16. In a similar way, the strip 14 near that flap 16' on panel 13 is parallel to the fold line 15', and the others 14, 14', which are parallel to each other, are inclined with respect to the strip 14 of the end on the side of the flap 16. The plastic-foam strips 14, 14' are provided with a plurality of suture-retaining slots 19.

FIG. 2 illustrates the package of FIG. 1 after the first panel 11 is folded over the interconnecting panel 12 and the second panel 13 is folded over the first panel 11, displaying sutures 23 and 24 in the stretched position of panels 11 and 13 between the edges of panel 12 and the fold lines 15, 15'.

FIG. 3 illustrates the package 10 of FIGS. 2 and 3 with the cover flaps 16 and 16' folded along the fold lines 15, 15', respectively, to cover the needle-displaying areas and the package closed by fitting tabs 17 and 17' into the slots 18 and 18'.

As illustrated in FIG. 2, the open package is in planer view with the ends provided with needles of the sutures in two rows. The needles are easily picked up with a needle-holder or the hand so as to remove the sutures from the package.

The packages of the present invention are preferably made of a heavy cardboard that can be stamped into the desired embodiment and provided with grooves for folding. Other folding thin materials such as sheet plastic or rigid plastic foams can be used instead of the desired cardboard. The foram strips 14, 14' are preferably 5 to 10 mm broad, at least 3 mm thick and are grooved in a depth of about 1 to 2 mm. The foam strips are more appropriately glued in position on the panels. A preferred foam is a high-density polyethylene, although other materials can also be used with good results. Alternatively, the needles can be mounted by perforating a solid resilient polymeric strip or a foam, although said needle-mounting technique makes the needles less appropriate for removal from the package.

Other variations in the construction or arrangement of the package as exposed here with be obvious to those skilled in he art. For instance, it will be seen that sutures can be package with needles mounted in the needle-display area and the remainder of the suture contained in the interior of the package. It can also be appropriate to mount the sutures upon only one panel, where there should be, for instance, only sutures for surgeries with two, three or more by passes. Many other variations of the present invention that employ the single-piece three-panel folded construction and the characteristics of presentation and display of the needles in two rows of the packages of the present invention will be obvious to those skilled in the art, and said variations will consequently be within the scope of the present invention.

I claim:

1. A suture package of the folded type suitable for holding a plurality of sutures with a needle affixed to at least one end of the suture, characterized by comprising;
    a first suture mounting panel (11) having a first supporting and holding element (14) attached thereto adjacent one end of said mounting panel (11) and adapted to hold a suture (23) at a position immediately adjacent to the needle (24);
    a second suture mounting panel (13) having a second supporting and holding element (14) attached thereto adjacent to one end of said second mounting panel (13) and adapted to hold a suture (13) at a position immediately adjacent to the needle (24);
    an interconnecting panel (12) connecting said first (11) and second (13) mounting panels;
    said first holding element (14) attached to said first suture mounting panel (11) at the opposite end of the package from said second holding element (14) on said second suture mounting panel (13);
    each suture mounting panel (11,13) possessing at least one additional supporting and holding element (14') and adapted to fix a suture thread along said suture mounting panel;
    each suture mounting panel (11, 13) being formed with a cover flap (16,16') adapted to fold over and enclose the needles (23) when the loaded package is folded to enclose the suture threads.

2. The package of claim 1, wherein said interconnecting panel (12), said first (11) and second (13) suture mounting panels are all the same width.

3. The package of claim 2 where one free edge of said first suture mounting panel (11) is provided with at least one tab (17), and further including at least one slot (18) in said interconnecting panel (12) aligned with said tab (17) in said first suture mounting panel (11) to hold said first suture mounting panel (11) in position over said interconnecting panel (12) when one is folded over the other.

4. The package of claim 1 wherein said additional supporting and holding element (14') on said first suture mounting panel (11) is aligned at an angle to said first supporting and holding element (14).

5. The apparatus claim 1 when said additional supporting and holding element (14') one said second suture mounting panel (13) is aligned at an angle to said second supporting and holding element (14).

6. The package of claim 1 further including at least one suture (23) with a needle (24) attached mounted on each of said first and second suture mounting panels (11,13) by fixing the needle (24) or the suture (23) immediately adjacent to the needle (24) on the respective first and second supporting and holding elements (14) and fixing the suture thread to each of said additional supporting and holding elements (14') on each of said respective first and second suture mounting panels (11,13).

* * * * *